US 6,485,941 B1

(12) United States Patent
Waldrop et al.

(10) Patent No.: US 6,485,941 B1
(45) Date of Patent: Nov. 26, 2002

(54) INHIBITION OF THE CARBOXYLTRANSFERASE COMPONENT OF ACETYL-COA CARBOXYLASE, AND THE USE OF SUCH INHIBITION IN ANTI-CANCER AND ANTI-LIPOGENIC THERAPIES

(75) Inventors: Grover L. Waldrop, Baton Rouge, LA (US); Jacqueline M. Stephens, Baton Rouge, LA (US); Keith L. Levert, Baton Rouge, LA (US)

(73) Assignee: Board of Supervisors of Louisiana State University and Agricultural and Mechanical College, Baton Rouge, LA (US)

( * ) Notice: Subject to any disclaimer, the term of this patent is extended or adjusted under 35 U.S.C. 154(b) by 0 days.

(21) Appl. No.: 10/128,038

(22) Filed: Apr. 23, 2002

(51) Int. Cl.⁷ .......................... C12N 15/09; C12N 9/00; C12N 9/88; C07F 9/06
(52) U.S. Cl. ...................... 435/69.2; 435/183; 435/232; 435/4; 435/15; 548/113; 548/303.7; 424/94.5
(58) Field of Search ................................ 435/69.2, 183, 435/232, 4, 15; 548/113, 303.7; 424/94.5

(56) References Cited

U.S. PATENT DOCUMENTS 6,242,610 B1    6/2001    Strongin et al. ......... 548/303.7

OTHER PUBLICATIONS

Abu–Elheiga, L. et al., "Continuous Fatty Oxidation and Reduced Fat Storage in Mice Lacking Acetyl–CoA Carboxylase 2," *Science 291*, 2613–2616 (2001).
Amspacher et al., "Synthesis of a Reaction Intermediate Analogue of Biotin–Dependent Carboxylases via a Selective Derivatization of Biotin," *Organic Lett. 1*, 99–102 (1999).
Blanchard, C. et al., *Biochemistry 38*, 3393–3400 (1999).
Blanchard, C. et al., "Overexpression and Kinetic Characterization of the Carboxyltransferase Component of Acetyl–CoA Carboxylase," *J. Biol. Chem. 273*, 19140–19145 (1998).
Bull, H. et al., "Mechanism–Based Inhibition of Human Steroid 5α–Reductase by Finasteride; Enzyme–Catalyzed Formation of NADP–Dihydrofinasteride, a Potent Bisubstrate Analog Inhibitor," *J. Am. Chem. Soc. 118*, 2359–2365 (1996).
Green, H. et al., "Spontaneous Heritable Changes Leading to Increased Adipose Conversion in 3T3 Cells," *Cell 7*, 105–113 (1976).
Green, H. et al., "Sublines of Mouse 3T3 Cells That Accumulate Lipid," *Cell 1*, 113–116 (1974).
Guchhait, R. et al., "Carboxyltransferase Component of Acetyl–CoA Carboxylase from *Escherichia Coli*," *Methods Enzymol 35*, 32–37 (1975).
Khalil, E. et al., "Mechanism–based inhibition of the melatonin rhythm enzyme: Pharmacologic exploitation of active site functional plasticity," *Proc. Nat. Acad. Sci. USA 96*, 12418–12423 (1999);.
Levert, K. et al., "A biotin analog inhibits acetyl–CoA carboxylase activity and adipogenesis," *J. Biol. Chem.*, vol. 277, 16347–16350 (2002).
Levert, K. et al., "A bisubstrate analog inhibitor of the carboxyltransferase component of acetyl–CoA carboxylase," *Biochem. Biophys. Res. Comm.*, vol. 291, pp. 1213–1217 (2002).
Li, S. et al., "The Gene Encoding the Biotin Carboxylase Subunit of *Escherichia coli* Acetyl–CoA Carboxylase," *J. Biol. Chem. 267*, 855–863 (1992).
Li, S. et al., "The Genes Encoding the Two Carboxyltransferase Subunits of *Escherichia coli* Acetyl–CoA Carboxylase," *J. Biol. Chem. 267*, 16841–16847 (1992).
Rozwarski, D. et al., *Science 279*, 98–102 (1998); and E. Khalil et al., *Proc. Nat. Acad. Sci. USA 96*, 12418–12423 (1999).
Thoden, J. et al., "Movement of the Biotin Carboxylase B–domain as a Result of ATP Binding," *J. Biol. Chem. 275*, 16183–16190 (2000).
Thupari, J. et al., "Fatty Acid Synthase Inhibition in Human Breast Cancer Cells Leads to Malonyl–CoA–Induced Inhibition of Fatty Acid Oxidation and Cytotoxicity," *Biochem. Biophys. Res. Commun. 285*, 217–223 (2001).
Waldrop, G. et al., "The synthesis of a bisubstrate inhibitor of ACC that inhibits adipocyte differentiation," *Poster Abstracts, Keystone Conference of Adipogenesis and Diabetes*, p. 102 (Keystone, CO, Jan. 2002).
Waldrop, G. et al., "Three–Dimensional Structure of the Biotin Carboxylase Subunit of Acetyl–CoA Carboxylase," *Biochemistry 33*, 10249–10256 (1994).
Waldrop,, G., K. Levert, and J. Stephens, "Synthesis and cell culture studies of a bisubstrate analog inhibitor of the carboxyltransferase component of acetyl CoA carboxylase," poster presentation, Gordon Research Conference (Jul. 23, 2001, Meriden, NH).

*Primary Examiner*—Tekchand Saidha
(74) *Attorney, Agent, or Firm*—John H. Runnels

(57) ABSTRACT

A method is disclosed for inhibiting carboxyltransferase with bisubstrate analogs. One such analog has been shown to inhibit the carboxyltransferase component of *E. coli* acetyl-CoA carboxylase. It is also expected to inhibit mammalian acetyl-CoA carboxylase, and thereby to act as an antiobesity agent and an anti-cancer agent.

10 Claims, 2 Drawing Sheets

Malonyl-CoA    Biotin

Compound 1

Compound 2

Compound 1

INHIBITION OF THE CARBOXYLTRANSFERASE COMPONENT OF ACETYL-COA CARBOXYLASE, AND THE USE OF SUCH INHIBITION IN ANTI-CANCER AND ANTI-LIPOGENIC THERAPIES

The development of this invention was partially funded by the Government under grant numbers GM51261 and R01DK5268-02 awarded by the National Institutes of Health. The Government has certain rights in this invention.

The synthesis of fatty acids in all animals, plants, and bacteria includes a step in which acetyl-CoA is carboxylated to form malonyl-CoA. This reaction is catalyzed by acetyl-CoA carboxylase, which uses biotin as a cofactor in a two-step mechanism:

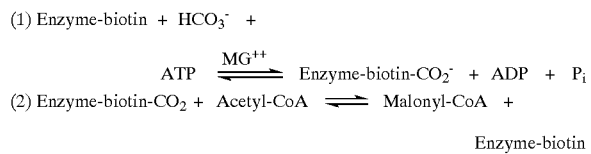

The first half-reaction is catalyzed by the biotin carboxylase component of acetyl-CoA carboxylase; this half-reaction involves the ATP-dependent carboxylation of biotin, using bicarbonate as a source of $CO_2$. In the second half reaction, which is catalyzed by the carboxyltransferase component of the enzyme, the carboxyl group is transferred from biotin to acetyl-CoA to form malonyl-CoA. In both half-reactions, biotin remains covalently bound to the enzyme through an amide bond to a specific lysine residue of the biotin carboxyl carrier protein. In *Escherichia coli*, biotin carboxylase, carboxyltransferase, and the biotin carboxyl carrier protein are three separate proteins, while in mammalian acetyl-CoA carboxylase these three components form separate domains within a single polypeptide.

The *E. coli* form of the enzyme has served as a model system for mechanistic studies of acetyl-CoA carboxylase, because both biotin carboxylase and carboxyltransferase retain their respective activities when isolated. Moreover, biotin carboxylase and carboxyltransferase both recognize free biotin as a substrate, eliminating the need for the biotin carboxyl carrier protein during kinetic studies. Most of the recent mechanistic studies of acetyl-CoA carboxylase have focused on the biotin carboxylase component, because its gene has been cloned and overexpressed. See S. Li et al., *J. Biol. Chem.* 267, 855–863 (1992); C. Blanchard et al., *J. Biol. Chem.* 273, 19140–19145 (1998); see also C. Blanchard et al., *Biochemistry* 38, 3393–3400 (1999). The three-dimensional structure of biotin carboxylase has been determined by x-ray crystallography, as has the three-dimensional structure of biotin carboxylase complexed to ATP. See G. Waldrop et al., *Biochemistry* 33, 10249–10256 (1994); J. Thoden et al., *J. Biol. Chem.* 275, 16183–16190 (2000). Relatively little work has focused on the carboxyltransferase component, however. Carboxyltransferase is an $\alpha_2\beta_2$ tetramer. Although the genes for the $\alpha$ and $\beta$ subunits of carboxyltransferase have been cloned, a system for the overexpression of these genes has been developed only recently. See S. Li et al., *J. Biol. Chem.* 267, 16841–16847 (1992); C. Blanchard et al., *J. Biol. Chem.* 273, 19140–19145 (1998). The overexpression system allows production of an ample supply of carboxyltransferase for structure/function studies.

Steady-state kinetic studies of recombinant carboxyltransferase have found a sequential mechanism in which both substrates must bind to the enzyme before catalysis occurs. C. Blanchard et al., *J. Biol. Chem.* 273, 19140–19145 (1998). The initial reaction rates (in the reverse direction as depicted in reaction (2) above) were consistent with an equilibrium-ordered kinetic mechanism, with malonyl-CoA binding before biotin. Note that carboxyltransferase from *E. coli* is routinely assayed in the non-physiological direction because of the availability of a facile spectrophotometric continuous assay that couples the production of acetyl-CoA with the reduction of $NAD^+$ by the combined reactions of citrate synthase and malate dehydrogenase. C. Blanchard et al., *J. Biol. Chem.* 273, 19140–19145 (1998); R. Guchhait et al., *Methods Enzymol* 35, 32–37 (1975). Carboxyltransferase assays also typically use biocytin in place of biotin, because biocytin gives reaction rates about three orders of magnitude higher than those for unmodified biotin. (Biocytin is biotin that is modified by attaching a lysine to the carboxyl group of the valeric acid side chain via an amide linkage with the $\epsilon$-amino group.)

Mice lacking a gene coding for one form of acetyl-CoA carboxylase have been observed to lose weight despite increased food consumption. See L. Abu-Elheiga et al., *Science* 291, 2613–2616 (2001). Abu-Elheiga et al. and J. Thupari et al, *Biochem. Biophys. Res. Commun.* 285, 217–223 (2001) have suggested that mammalian acetyl-CoA carboxylase might be a potential target for anti-obesity or anti-cancer drugs, respectively.

Adipocytes are highly specialized cells that play a central role in lipid homeostasis and energy balance. Obesity, an excessive accumulation of adipose tissue, is a major risk factor in the development of Type II diabetes, cardiovascular disease, and hypertension. Recent studies have indicated that obesity and Type II diabetes may be correlated with a breakdown in the regulatory mechanisms that control adipocyte gene expression.

We have discovered a method to inhibit carboxyltransferase using bisubstrate analogs. The structure of one such bisubstrate analog (Compound 1) of carboxyltransferase is shown in FIG. 1, along with the substrates malonyl-CoA and biotin. Compound 1 has been synthesized, and has been shown to inhibit the carboxyltransferase component of *E. coli* acetyl-CoA carboxylase. Compound 1 also inhibits mammalian acetyl-CoA carboxylase, and thereby could act as an antiobesity agent and an anti-cancer agent.

Since Compound 1 includes the nucleotide ADP, the cell membrane is impermeable to Compound 1. However, a precursor to Compound 1, the chloroacetylated (or haloacetylated) biotin derivative Compound 2 (see FIG. 2), is sufficiently hydrophobic to diffuse across the cell membrane. Moreover, we have shown that Compound 2 inhibits adipocyte differentiation and gene expression.

This bisubstrate analog will be useful in the treatment and prevention of obesity and diabetes.

Cancer cells also typically have high levels of fatty acid synthesis. Inhibitors of fatty acid synthesis are in clinical trials for the treatment of breast cancers. Since acetyl-CoA carboxylase—not fatty acid synthase—is the rate-limiting enzyme in fat synthesis, the inhibition of acetyl-CoA carboxylase with the bisubstrate analog could be even more effective in treating cancers than are inhibitors of fatty acid synthesis.

ABBREVIATIONS

Figure 1:
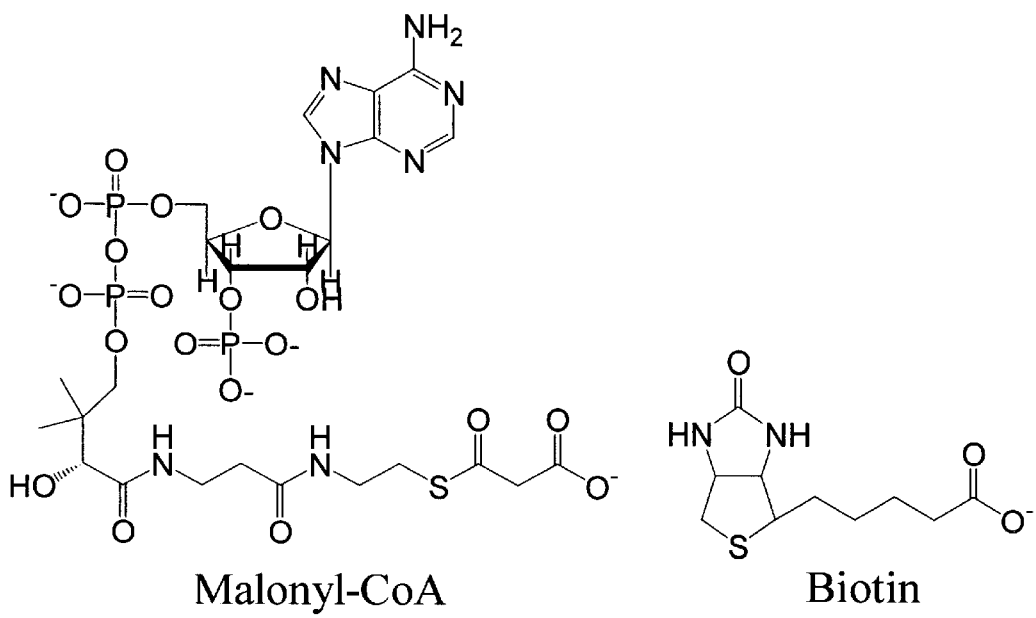
FIG. 1 depicts the structures of malonyl-CoA, biotin, and the bisubstrate analog inhibitor Compound 1.
Figure 1:
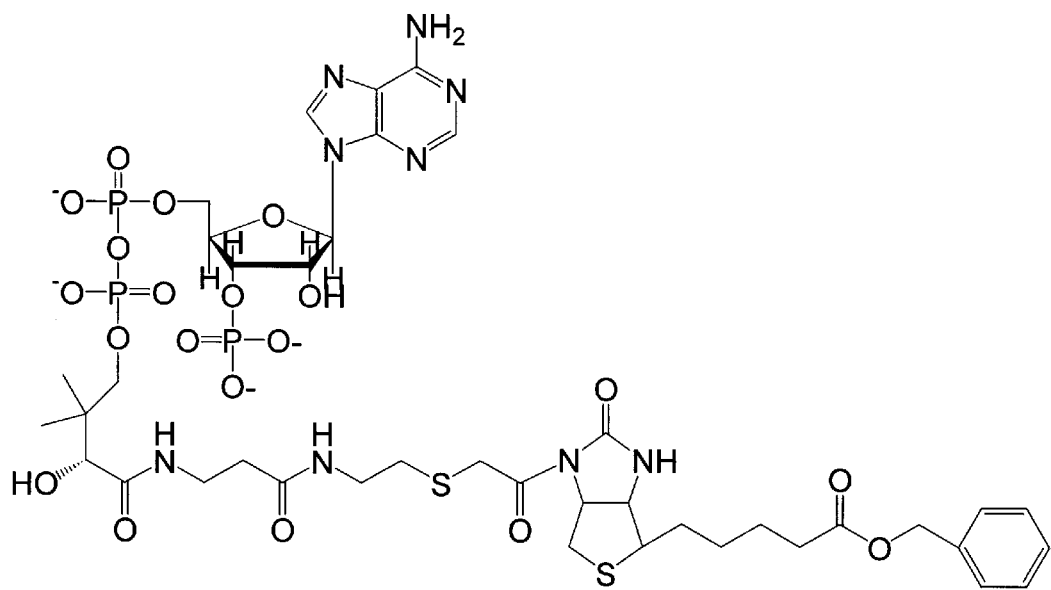

Abbreviations used in the specification and Claims include the following:
PPAR—peroxisome proliferator-activated receptor
STAT—signal transducer and activator of transcription
FBS—fetal bovine serum
MIX—3-isobutyl-1-methylxanthine
DEX—dexamethasone
DMEM—Dulbecco's Modified Eagle's Medium
HRP—horseradish peroxidase
DMSO—dimethyl sulfoxide

Materials and Methods

Materials

Dulbecco's Modified Eagle's Medium (DMEM) was purchased from Life Technologies (Grand Island, N.Y.). Bovine and fetal bovine serum (FBS) were obtained from Sigma (St. Louis, Mo.) and Life Technologies, respectively. PPARγ was a mouse monoclonal antibody from Santa Cruz (Santa Cruz, Calif.). STAT antibodies were monoclonal IgGs purchased from Transduction Laboratories (San Diego, Calif.) or polyclonal IgGs purchased from Santa Cruz. Streptavidin linked to horseradish peroxidase (HRP) was purchased from Pierce (Rockford, Ill.). His-binding resin was purchased from Novagen (Madison, Wis.). HPLC was performed using a Waters HPLC system (Milford, Mass.) equipped with a Waters 996 photodiode array detector. Preparative HPLC was performed with a Waters AP-1 glass column (1 cm×20 cm) packed with Bondapak C-18, 15–20 μm, also purchased from Waters. Analytical HPLC was performed with a Discovery C-18 column (15 cm×4 mm, 5 μm) purchased from Supelco (Bellefonte, Pa.). All NMR spectra were recorded on Bruker (Billerica, Mass.) spectrometers; 400 MHz for $^1$H and $^{31}$P NMR spectra, and 500 MHz for $^{13}$C NMR spectra. All other reagents were purchased from Sigma or Aldrich (Milwaukee, Wis.). Except as otherwise stated, all reagents were used as received.

Synthesis of Bisubstrate Analog

Compound 2 was synthesized as described in D. Amspacher et al., *Organic Lett.* 1, 99–102 (1999); and U.S. Pat. No. 6,242,610. Compound 1 was synthesized by reacting Compound 2 with coenzyme A (Sigma). Coenzyme A (1 equivalent) was dissolved in a solution of 1 M triethylammonium bicarbonate buffer (50 mL of buffer (pH 8.5) per mmol of coenzyme A). This solution was then added to a solution of Compound 2 (5 equivalents) in MeOH (20 mL of MeOH per mmol of Compound 2) that had been freshly degassed by bubbling with $N_2$. The mixture of the two solutions was stirred under $N_2$ for 12 hours. The reaction mixture was then concentrated in vacuo to remove MeOH. The remaining aqueous solution was diluted with $H_2O$ to ~15 mL, and was extracted with ethyl acetate (2×15 mL) to remove unreacted Compound 2. The remaining solution was lyophilized, and then purified by HPLC. The HPLC used as mobile phases: 10 mM $KH_2PO_4$, pH 6.7 (A), and MeOH (B). The flow rate was 2 mL/min with the following gradient: 100% A at zero time, followed by a linear gradient to 30% B over 60 min, hold at 30% B for 60 min, followed by a linear gradient to 100% B over the next 20 min. Using this gradient the retention time for Compound 1 was generally around 122 to 128 min. Compound 1 was lyophilized to dryness and was quantified by UV absorption at 259.5 nm based on the extinction coefficient for Coenzyme A (16,800 $M^{-1}$ $cm^{-1}$). $^1$H NMR ($D_2O$): δ8.57, (s, 1H), 8.27, (s, 1H), 7.44, (s, 5H), 6.18, (d, J=7.1 Hz, 1H), 5.19, (m, 2H), 4.58, (s, 1H) 4.24, (s, 2H), 4.04, (m, 1H), 3.99, (s, 2H), 3.86, (s, 2H), 3.83, (s, 1H), 3.80, (m, 1H) 3.56, (m, 1H), 3.48, (m, 2H), 3.39, (m, 2H), 3.30, (m, 1H), 3.09–2.96, (m, 2H), 2.75, (t, J=6.5 Hz, 2H), 2.47, (m, 4H), 1.94, (s, 1H), 1.68–1.20, (m, 6H), 0.90, (s, 3H), 0.75, (s, 3H); $^{13}$C NMR ($D_2O$): δ176.97, 175.31, 174.45, 172.10, 157.76, 156.20, 153.38, 149.87, 140.37, 136.25, 129.36, 128.98, 119.22, 87.14, 84.31, 74.79, 74.39, 72.43, 67.41, 66.18, 62.57, 60.96, 58.48, 55.86, 55.19, 52.72, 39.21, 38.85, 37.75, 35.99, 34.98, 34.27, 31.66, 28.15, 27.78, 24.54, 21.47, 18.69, 8.84; $^{31}$P NMR ($D_2O$): δ3.04, −11.84, −12.26. Matrix assisted laser desorption ionization MS: calculated for $[C_{40}H_{58}N_9O_{20}P_3S_2+K^+]$, 1180.08; observed, 1180.03; also observed were peaks at 1218.85, 1256.92, and 1294.92, corresponding to adducts containing 2, 3, and 4 potassium ions, respectively.

Cell Culture

Murine 3T3-L1 pre-adipocytes (a kind gift from Howard Green, Harvard University, Cambridge, Mass.) were plated and grown to 2 days post-confluence in DMEM supplemented with 10% bovine serum. Medium was changed every 48 hours. Cells were induced to differentiate into adipocytes by changing the medium to DMEM supplemented with 10% fetal bovine serum (FBS), 0.5 mM 3-isobutyl-1-methylxanthine (MIX) (Sigma), 1 μM dexamethasone (DEX) (Sigma), and 1.7 μM insulin (Sigma). After 48 hours this medium was replaced with DMEM supplemented with 10% FBS, and the cells were maintained in this medium until they were used in experiments. Compound 2 was dissolved in DMSO and added to the cell culture media at a 1:1000 dilution for experiments. Vehicle additions were also conducted for each experiment as controls.

Preparation of Whole Cell Extracts

Monolayers of 3T3-L1 adipocytes were rinsed with phosphate-buffered saline (PBS) and then harvested in a non-denaturing buffer containing 150 mM NaCl, 10 mM Tris, pH 7.4, 1 mM EGTA, 1 mM EDTA, 1% Triton-X 100, 0.5% Nonidet P-40 detergent (Sigma), 1 μM PMSF (phenylmethylsulfonyl fluoride protease inhibitor, Sigma), 1 μM pepstatin (Sigma), 50 trypsin inhibitory milliunits of aprotinin (Sigma), 10 μM leupeptin (Sigma), and 2 mM sodium vanadate (Fisher Chemical, Fair Lawn, NH) for Western blot analysis. Samples were extracted for 30 minutes on ice and centrifuged at 10,000 g at 4° C. for 15 minutes. Supernatants containing whole cell extracts were analyzed for protein content using a BCA kit (Pierce) according to the manufacturer's instructions.

The above procedure was modified to prepare extracts for enzymatic analysis. The non-denaturing buffer in that case contained 150 mM KCl instead of NaCl, and there was no Triton X-100, Nonidet P-40, nor any protease or phosphatase inhibitors in the buffer. The cell monolayers were scraped into this buffer, and were homogenized with 16 strokes in a Dounce homogenizer. The homogenates were centrifuged at 10,000 g for 5 minutes, and the supernatants were saved as cytosolic extract, quantitated, and used to assay acetyl-CoA carboxylase activity.

Gel Electrophoresis and Immunoblotting

Proteins were separated in 5%, 7.5%, or 12% polyacrylamide (National Diagnostics, Hercules, Calif.) gel containing sodium dodecyl sulfate (SDS) following the procedure of U. Laemmli, *Nature* 227, 680–685 (1970). Proteins were then transferred to nitrocellulose (BioRad, Atlanta, Ga.) in 25 mM Tris, 192 mM glycine, and 20% methanol. Following transfer, the membrane was blocked in 4% milk (non-fat, dried milk reconstituted in water at a 4% concentration (w/v)) for 1 hour at room temperature. Results were visualized with horseradish peroxidase (HRP)-conjugated secondary antibodies (Sigma) and enhanced chemiluminescence (Pierce).

Enzyme Assays

Carboxyltransferase was purified from a strain of *E. coli* that overexpresses the genes encoding the α and β subunits of the enzyme. C. Blanchard et al., *J. Biol. Chem.* 273, 19140–19145 (1998). (*E. coli* strain available on request from G. Waldrop, Department of Biological Sciences, Louisiana State University, Baton Rouge, La.) The published procedure was modified slightly. Bacteria were grown to saturation at 37° C. in 1 L of LB medium in 2 L flasks, and were then induced with 1 g of lactose and incubated without shaking at 25° C. for 24 h. The concentration of carboxyltransferase was determined by the method of M. Bradford, *Anal. Biochem.* 72, 248–254 (1976) using bovine serum albumin as a standard.

Carboxyltransferase was assayed in the reverse direction: the production of acetyl-CoA was detected by using the coupling enzymes malate dehydrogenase and citrate synthase, and the reduction of NAD$^+$ was measured spectrophotometrically by the method of C. Blanchard et al., *J. Biol. Chem.* 273, 19140–19145 (1998); and R. Guchhait et al., *Methods Enzymol.* 35, 32–37 (1975).

The bisubstrate analog had previously been observed not to inhibit the activity of either of these coupling enzymes at 0.6 mM, a value three times higher than the highest concentration used in the inhibition studies. That the bisubstrate analog did not inhibit either coupling enzyme was determined by measuring the reduction of NAD$^+$ following the addition of a sub-saturating concentration of acetyl-CoA (in place of carboxyltransferase) to the reaction mixture, both with and without the bisubstrate analog. No decrease in activity was observed in the presence of 0.6 mM of Compound 1, indicating that neither coupling enzyme had been inhibited.

The activity of acetyl-CoA carboxylase from 3T3-L1 cell lysates was determined in a fixed-time assay using HPLC. HPLC is not normally used in this field, because cell lysates are mixtures of such a large number of different components; it would be more conventional to use an assay employing radioactivity. Surprisingly, we have discovered an HPLC-based assay that performed well for these measurements, and that is more specific and accurate. This assay will be useful in monitoring the progress and reaction of patients who are administered treatment in accordance with this invention.

Assays were performed by measuring the loss of acetyl-CoA, or the production of malonyl-CoA, at 5 minute intervals for 20 minutes, using reverse-phase HPLC. The rate of conversion of acetyl-CoA to malonyl-CoA was found to be approximately linear over a period of 20 minutes. Rates were calculated by linear regression analysis of malonyl-CoA concentration as a function of time. The reaction mixture contained 50 mM Tris, pH 7.5, 6 μM Acetyl-CoA, 2 mM ATP, 7 mM KHCO$_3$, 8 mM MgCl$_2$, 1 mM DTT, and 1 mg/mL bovine serum albumin. Cell lysates were pre-incubated (30 min, 25° C.) with bovine serum albumin (2 mg/mL) and potassium citrate (10 mM). Reactions were initiated by transferring 50 μL of pre-incubated cell lysate to the reaction mixture (final volume 200 μL), followed by incubation for 5–20 min at 25° C. Reactions were terminated by the addition of 50 μL 10% perchloric acid. Following termination of the reaction, the samples were centrifuged (3 min, 10,000 g) and then analyzed by HPLC. A mobile phase of 10 mM KH$_2$PO$_4$, pH 6.7 (A) and MeOH (B) was used. The flow rate was 1.0 mL/min, at the following gradient: hold at 100% A for 1 min, followed by a linear gradient to 30% B over the next 5 min, then hold at 30% B for 5 min. The observed retention times were 7.5 and 9.0 min for malonyl-CoA and acetyl-CoA, respectively.

Data Analysis

Data for competitive and noncompetitive inhibition were fit to Equations [1] and [2], respectively. In Equations [1] and [2], v is the initial velocity, $V_m$ is the maximal velocity, A is the substrate concentration, I is the concentration of inhibitor, $K_m$ is the Michaelis constant, $K_{is}$ is the slope inhibition constant, and $K_{ii}$ is the intercept inhibition constant.

$$v = V_m A/(K_m(1+I/K_{is})+A) \quad [1]$$

$$v = V_m A/(K_m(1+I/K_{is})+A(1+I/K_{ii})) \quad [2]$$

Results and Discussion

Synthesis of the Bisubstrate Analog for Carboxyltransferase.

Figure 2:
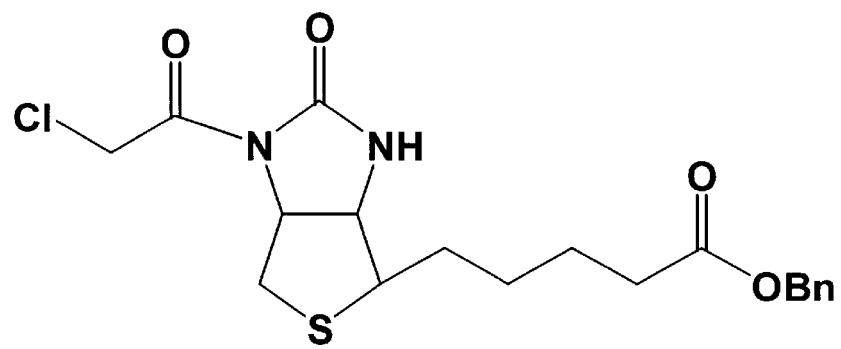
FIG. 2 depicts schematically the alkylation reaction between Coenzyme A and the chloroacetylated biotin analog Compound 2, forming the bisubstrate analog inhibitor Compound 1.
Figure 2:
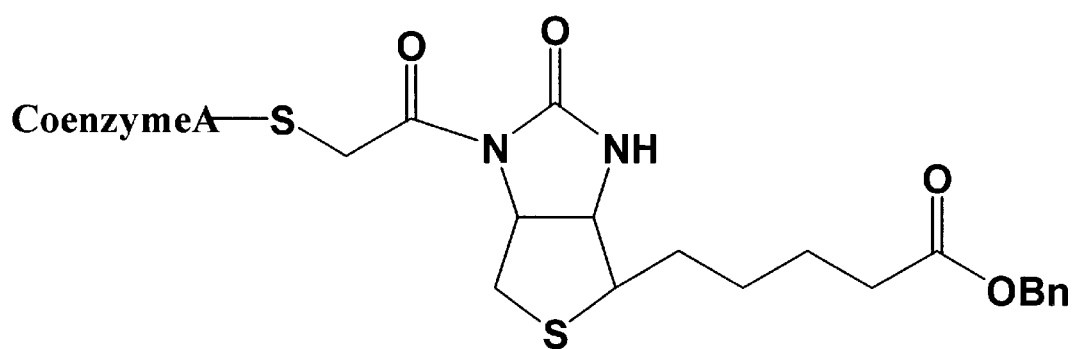

Carboxyltransferase catalyzes the transfer of a carboxyl group from the 1'-N of biotin to acetyl-CoA to form malonyl-CoA. The bisubstrate analog was synthesized by covalently linking Coenzyme A to the 1'-N position of biotin via an acyl bridge, as shown schematically in FIG. 2.

Synthesis of the bisubstrate analog proceeded through intermediate Compound 2. Because primary sulfur atoms are strong nucleophiles, and Compound 2 has an electrophilic carbon adjacent to a carbonyl group, the chloride in Compound 1 was readily substituted with the sulfur of Coenzyme A to produce Compound 2. The reaction was carried out in triethylammonium bicarbonate buffer, pH 8.5, at room temperature. The bisubstrate analog was purified by extraction and reverse phase HPLC. Spectroscopic analysis ($^1$H, $^{13}$C, and $^{31}$P NMR, and mass spectrometry) verified the structure of bisubstrate Compound 1. Since removal of the benzyl protecting group from the valeric acid side chain of biotin reduces the yield of the final product, and considering that the natural biotin substrate, in vivo, is attached to a small protein at the same site as this protecting group, we decided not to remove the benzyl protecting group from Compound 1 to increase yield, as that group should not significantly affect binding of the inhibitor. We observed that the enzyme did not appear to catalyze the synthesis of Compound 1. When carboxyltransferase, Coenzyme A, and Compound 2 were combined, the rate of formation of Compound 1 was the same as the rate in the absence of any carboxyltransferase.

Inhibition of Carboxyltransferase by the Bisubstrate Analog

The bisubstrate analog inhibited carboxyltransferase activity. The activity of carboxyltransferase was measured in the reverse direction using malonyl-CoA and biocytin as substrates. The inhibition of carboxyltransferase by Compound 1 was observed by varying malonyl-CoA concentration at different concentrations of inhibitor, with biocytin concentration held constant at a sub-saturating level, 6.0 mM. The inhibition was also observed by varying biocytin concentration at different concentrations of Compound 1, with malonyl-CoA concentration held constant at a sub-saturating level, 0.1 mM. With malonyl-CoA as the variable substrate, Compound 1 exhibited competitive inhibition. The observed data were fit to equation [1] to give an inhibition constant ($K_{is}$) of 23±2 $\mu$M. When biocytin was the variable substrate, noncompetitive inhibition was observed.

The competitive inhibition pattern for malonyl-CoA, and the noncompetitive inhibition pattern for biocytin indicate an equilibrium-ordered addition of the substrates to carboxyltransferase, in which malonyl-CoA binds first, consistent with the observations of C. Blanchard et al., *J. Biol. Chem.* 273, 19140–19145 (1998). An equilibrium-ordered mechanism also indicates that the off-rate constants for the substrates are greater than the forward rate constants for forming products. Therefore, the $K_m$ values for malonyl-CoA and biocytin are equal to or very close to the dissociation constants of the substrates for the enzyme. Using the $K_m$ values for the two substrates (malonyl-CoA: 0.1 mM and biocytin: 8 mM) as dissociation constants, the product of the dissociation constants for the two substrates is greater than the inhibition constant (23 $\mu$M) for Compound 1 by a factor of about 35. This result is consistent with a mechanism in which the inhibitor induces a conformational change in the enzyme. If the bisubstrate analog did not induce a conformational change, then the binding energy of the inhibitor should simply be the sum of the binding energies of the two substrates, and the $K_{is}$ should simply equal the product of the dissociation constants for the two substrates. These results show that the binding energy of the bisubstrate inhibitor is about 1.3 times less than the sum of the binding energies of the two substrates individually.

Effects on Adipocyte Differentiation

Obesity is characterized by an increase in both the number and the size of adipocytes. Mice treated with inhibitors of fatty acid synthase have been observed to exhibit weight loss and decreased food intake. Because acetyl-CoA carboxylase is involved in the first step in fatty acid synthesis in mammals, that enzyme is a target for anti-obesity therapeutics. The activity of acetyl-CoA carboxylase is known to increase during adipogenesis. The bisubstrate analog inhibitor of the carboxyltransferase component of acetyl-CoA carboxylase is therefore expected to be useful as an anti-lipogenic agent. Since Compound 1 contains the nucleotide ADP, it is too hydrophilic to cross the plasma membrane. However, the chloroacetylated (or haloacetylated) biotin precursor (e.g., Compound 2 in FIG. 2) is sufficiently hydrophobic to cross the plasma membrane. Upon entering the cell, Compound 2 will react with endogenous Coenzyme A to form the bisubstrate analog 1. The intracellularly-formed bisubstrate analog then inhibits either the cytosolic or the mitochondrial isoform of acetyl-CoA carboxylase, or both, and thereby attenuates the accumulation of triacylglycerol in adipocytes.

Alternatively, or in addition, Compound 1 or Compound 2 is administered in dosages and for a time to increase to a statistically significant degree the overall energy expenditure or consumption of the mammal, whereby the total mass of adipocytes in the mammal decreases to a statistically significant degree.

In other contexts, other workers have caused the formation of enzyme inhibitors intracellularly by reaction of a precursor with a metabolite. Examples include finasteride, which inhibits 5α a reductase; isoniazid, which inhibits the mycobacterial enzyme InhA; and a bisubstrate analog inhibitor of serotonin N-acetyltransferase. See H. Bull et al., *J. Am. Chem. Soc.* 118, 2359–2365 (1996); D. Rozwarski et al., *Science* 279, 98–102 (1998); and E. Khalil et al., *Proc. Nat. Acad. Sci. USA* 96, 12418–12423 (1999); respectively. The first two examples are used clinically to treat benign prostatic hypertrophy and tuberculosis, respectively. It was suggested that the third might be useful in therapies for sleep and mood disorders.

The murine 3T3-L1 pre-adipocyte cell line was used to examine the effects of Compound 2 on adipocyte differentiation. The 3T3-L1 cell line can be induced to differentiate in culture from fibroblasts, or pre-adipocytes, into cells with the morphological and biochemical properties of adipocytes. See H. Green et al., *Cell* 1, 113–116 (1974); and H. Green et al., *Cell* 7, 105–113 (1976) The 3T3-L1-derived adipocytes are comparable to native adipocytes. For example, these cells accumulate lipids, respond to insulin, and secrete leptin. The 3T3-L1 pre-adipocytes were first grown to a confluent monolayer. At two days post-confluence, the cells were exposed to a "differentiation cocktail" (FBS, MIX, DEX, and insulin) for 48 hours, and the cells were then maintained in 10% FBS in DMEM in the presence or absence of various doses of Compound 2. A vehicle addition of DMSO was also performed as a control. Compound 2 or DMSO was added in a 1-to-1000 dilution to the cell culture medium every 24 hours. One week after treatment with the differentiation cocktail, whole cell extracts were prepared, and cells were stained with Oil Red O to assess lipid accumulation.

The differentiation of pre-adipocytes into adipocytes has been attributed, in part, to increased expression of several transcription factors, including PPARγ and STATs 1, 5A, and 5B. To observe the differentiation of pre-adipocytes into adipocytes, the expression of these transcription factors was examined by Western blot analysis (data not shown). Adipogenesis was also assessed by examining lipid accumulation, as judged by Oil Red O staining (data not shown).

We found that Compound 2 inhibited adipocyte differentiation of 3T3-L1 cells in a dose-dependent manner. Whole cell extracts were prepared one week after the induction of differentiation in the presence of 0, 1, 2, 4, 8, or 17 $\mu$M doses of Compound 2, or treatment with DMSO (vehicle), with treatments in each case repeated every 24 hours. 100 $\mu$g of each extract was separated by SDS-PAGE, transferred to nitrocellulose, and subjected to Western blot analysis. The detection system was horseradish peroxidase-conjugated secondary antibodies (Sigma) and enhanced chemiluminescence (Pierce).

We also observed the effects of Compound 2 on lipid accumulation during 3T3-L1 adipocyte differentiation. Cells were induced to differentiate at 2 days post-confluence. 0, 4, 8, and 17 $\mu$M concentrations of Compound 2 were added at the start of differentiation. After 48 hours, the induction medium was replaced with DMEM. Once cells had been exposed to Compound 2, the cells were treated every 24 hours with a fresh bolus of Compound 2 or of DMSO vehicle. One week after 3T3-L1 cells were induced to differentiate, they were stained with Oil Red O and observed visually.

Optimal differentiation (essentially 100%), as judged by PPARγ expression and Oil red O staining, was achieved when 3T3-L1 cells were exposed to the usual differentiation cocktail of FBS, MIX, DEX, and insulin. We also observed a dose-dependent inhibition of the differentiation of these cells in the presence of Compound 2. Exposing pre-adipocytes to 17 μM or 8 μM of Compound 2 blocked the induction of PPARγ expression as monitored by Western blotting, and also blocked lipid accumulation as judged by Oil Red O staining. Likewise, STATs 1 and 5A were strongly expressed during induced differentiation, and the expression of both of these transcription factors was also inhibited in a dose-dependent manner by Compound 2. However, levels of STAT3, a protein whose expression is not significantly regulated during differentiation, was unaffected by treatment with Compound 2. The observation that STAT3 expression was unaffected by Compound 2 is significant, as it shows that Compound 2 did not act simply as a non-specific alkylating agent. Instead, these data show that Compound 2 affected the expression of adipogenesis-specific genes. We also observed that inhibition of differentiation by Compound 2 was reversible. When Compound 2 was not added at 24 hour intervals following initial treatment, the cells started to differentiate into adipocytes.

We also examined whether there was a concomitant decrease in the activity of acetyl-CoA carboxylase. To determine acetyl-CoA carboxylase activity in cells treated with Compound 2, cell lysates were prepared from pre-adipocytes that had been treated with Compound 2 (10 μM) for four hours. Acetyl-CoA carboxylase activity was measured by analytical reverse phase HPLC. The activity of acetyl-CoA carboxylase from cells treated with Compound 2 was 0.30 nmol malonyl-CoA/min-mg, while cells treated with DMSO had an activity of 1.40 nmol/min-mg. A Western Blot probe with streptavidin linked to HRP showed equal amounts of enzyme in both treated and untreated cells (data not shown), confirming that the decrease in activity was not due to a decrease in the concentration of cellular acetyl-CoA carboxylase. Thus, treatment of pre-adipocytes with Compound 2 (10 μM) produced both a substantial decrease in acetyl-CoA carboxylase activity and a substantial decrease in adipogenesis.

Without wishing to be bound by this theory, we believe that Compound 2 reacts to form Compound 1 intracellularly, since the only primary thiol other than Coenzyme A that is present in the cytosol at any appreciable concentration is glutathione, and available data suggest that glutathione does not cause appreciable interference.

We have also found that, like the bacterial enzyme, the murine version of acetyl-CoA carboxylase does not appear to catalyze the formation of Compound 1. However, when the bisubstrate analog 1 was added to cell-free extracts of pre-adipocytes, it inhibited murine acetyl-CoA carboxylase activity, while Compound 2 did not. In other words, Compound 2 had no effect on acetyl-CoA carboxylase activity in vitro, but it did when added in vivo.

Studies are underway to determine whether a glutathione-biotin adduct will inhibit acetyl-CoA carboxylase, and to detect Compound 1 in extracts of pre-adipocytes treated with Compound 2. In experiments to date, we have not seen substantial reaction between glutathione and Compound 2.

One might ask how an inhibitor with a relatively modest 23 μM $K_i$ value can have such a significant biological effect. The answer begins with the observation that acetyl-CoA carboxylase is essential for cell growth. Gene knockout experiments by others have shown that the absence of the cytosolic isoform of acetyl-CoA carboxylase causes death in mice. If the goal is not to abolish the activity of acetyl-CoA carboxylase and kill the cell, but instead to attenuate the enzyme's activity to inhibit the accumulation of lipid, then a molecule with a 23 μM $K_i$ value can be quite useful, while a molecule with a nM or lower $K_i$ value could cause cell death.

Cancer cells also typically have high levels of fatty acid synthesis. Various inhibitors of fatty acid synthesis are currently in clinical trials for the treatment of breast cancers. Since acetyl-CoA carboxylase—not fatty acid synthase—is the rate-limiting enzyme in fat synthesis, the inhibition of acetyl-CoA carboxylase with the bisubstrate analog should be at least as effective in treating cancers as fatty acid synthesis inhibitors, if not more so. Preliminary data in the breast cancer cell line MCF7 have shown that Compound 2 inhibited cellular proliferation in that cell line in a dose-dependent manner, as judged by counting the number of viable cells as a function of time.

Miscellaneous

Compounds in accordance with the present invention may be administered to a patient for treatment of obesity or cancer by any suitable means, including oral, intravenous, parenteral, subcutaneous, intrapulmonary, and intranasal administration. Parenteral infusions include intramuscular, intravenous, intraarterial, or intraperitoneal administration. The compounds may also be administered transdermally, for example in the form of a slow-release subcutaneous implant, or orally in the form of capsules, powders, or granules. It may also be administered by inhalation.

Pharmaceutically acceptable carrier preparations for parenteral administration include sterile, aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. The active therapeutic ingredient may be mixed with excipients that are pharmaceutically acceptable and are compatible with the active ingredient. Suitable excipients include water, saline, dextrose, glycerol and ethanol, or combinations thereof. Intravenous vehicles include fluid and nutrient replenishers, electrolyte replenishers, such as those based on Ringer's dextrose, and the like. Preservatives and other additives may also be present such as, for example, antimicrobials, anti-oxidants, chelating agents, inert gases, and the like.

The form may vary depending upon the route of administration. For example, compositions for injection may be provided in the form of an ampule, each containing a unit dose amount, or in the form of a container containing multiple doses.

The compound may be formulated into therapeutic compositions as pharmaceutically acceptable salts. These salts include acid addition salts formed with inorganic acids, for example hydrochloric or phosphoric acid, or organic acids such as acetic, oxalic, or tartaric acid, and the like. Salts also include those formed from inorganic bases such as, for example, sodium, potassium, ammonium, calcium or ferric hydroxides, and organic bases such as isopropylamine, trimethylamine, histidine, procaine and the like.

Controlled delivery may be achieved by admixing the active ingredient with appropriate macromolecules, for example, polyesters, polyamino acids, polyvinyl pyrrolidone, ethylenevinylacetate, methylcellulose, carboxymethylcellulose, prolamine sulfate, or lactide/ glycolide copolymers. The rate of release of the active compound may be controlled by altering the concentration of the macromolecule.

Another method for controlling the duration of action comprises incorporating the active compound into particles of a polymeric substance such as a polyester, peptide, hydrogel, polylactide/glycolide copolymer, or ethylenevinylacetate copolymers. Alternatively, an active compound may be encapsulated in microcapsules prepared, for example, by coacervation techniques or by interfacial polymerization, for example, by the use of hydroxymethylcellulose or gelatin-microcapsules or poly(methylmethacrylate) microcapsules, respectively, or in a colloid drug delivery system. Colloidal dispersion systems include macromolecule complexes, nanocapsules, microspheres, beads, and lipid-based systems including oil-in-water emulsions, micelles, mixed micelles, and liposomes.

For both anti-obesity and anti-cancer therapeutics, initial in vivo animal trials will be conducted in accordance with all applicable laws and regulations, following by clinical trials in humans in accordance with all applicable laws and regulations.

In Compound 2, the chlorine atom may be replaced by another halogen atom. The formal nomenclature for this generalization of Compound 2 is phenylmethyl 5-(6,8-diaza-6-(2-X-acetyl)-7-oxo-3-thiabicyclo[3.3.0]oct-2-yl) pentanoate; wherein X is fluorine, chlorine, bromine, or iodine.

The formal nomenclature for Compound 1 is phenylmethyl 5-(1-{[(2-{[N-(2,4-dihydroxy-3,3-dimethylbutanyl)-5-(6-aminooctahydro-9H-purin-9-yl)-4-(hydroxy-2-[(phosphonooxy)tetrahydrofuran-2-yl]methyl dihydrogen diphosphate-β-alanyl]amino}ethyl)thio]acetyl}-2-oxohexahydro-1H-thieno[3,4-d]imidazol-4-yl)pentanoate.

"Statistical significance" is understood to refer to results that are significant at the P<0.05 level, or, where appropriate in context, such other measure of statistical significance as those of skill in the art would apply to particular experimental or clinical results.

The complete disclosures of all references cited in this specification are hereby incorporated by reference. Also incorporated by reference are the following instances of the inventors' own work, which are not prior art to this application: G. Waldrop, K. Levert, and J. Stephens, "Synthesis and cell culture studies of a bisubstrate analog inhibitor of the carboxyltransferase component of acetyl CoA carboxylase," poster presentation, Gordon Research Conference (Jul. 23, 2001, Meriden, N.H.); G. Waldrop et al., "The synthesis of a bisubstrate inhibitor of ACC that inhibits adipocyte differentiation," *Poster Abstracts, Keystone Conference of Adipogenesis and Diabetes*, p. 102 (Keystone, Colo., Jan. 2002); K. Levert et al., "A bisubstrate analog inhibitor of the carboxyltransferase component of acetyl-CoA carboxylase," *Biochem. Biophys. Res. Comm.*, vol. 291 pp. 1213–1217 (2002); and K. Levert et al., "A biotin analog inhibits acetyl-CoA carboxylase activity and adipogenesis," *J. Biol Chem.*, vol. 277, pp. 16367–16350 (2002). In the event of an otherwise irreconcilable conflict, however, the present specification shall control.

We claim:

1. A method for inhibiting the carboxyltransferase activity of acetyl-CoA carboxylase, comprising reacting the acetyl-CoA carboxylase with a composition comprising Compound 1:

phenylmethyl 5-(1-{[(2-{[N-(2,4-dihydroxy-3,3-dimethylbutanyl)-5-(6-aminooctahydro-9H-purin-9-yl)-4-(hydroxy-2-[(phosphonooxy)tetrahydrofuran-2-yl]methyl dihydrogen diphosphate-β-alanyl]amino}ethyl)thio]acetyl}-2-oxohexahydro-1H-thieno[3,4-d]imidazol-4-yl)pentanoate;

wherein the amount of the Compound 1 is sufficient to reduce the activity of carboxyltransferase by a statistically significant degree.

2. A method as recited in claim 1, wherein said reacting occurs in vivo in a mammal.

3. A method as recited in claim 2, wherein the mammal is a human.

4. A method as recited in claim 2, wherein the Compound 1 is generated in vivo by administering to the mammal a precursor of Compound 1 comprising phenylmethyl 5-(6,8-diaza-6-(2-X-acetyl)-7-oxo-3-thiabicyclo[3.3.0]oct-2-yl) pentanoate; wherein X is fluorine, chlorine, bromine, or iodine; whereby the precursor is metabolized to Compound 1 within cells of the mammal.

5. A method as recited in claim 4, wherein X is chlorine.

6. A method as recited in claim 2, wherein the composition is administered in dosages and for a time to reduce to a statistically significant degree the size of a tumor in the mammal.

7. A method as recited in claim 2, wherein the composition is administered in dosages and for a time to reduce to a statistically significant degree the number, size, or both of adipocytes in the mammal.

8. A method as recited in claim 7, wherein the composition is administered in dosages and for a time to increase to a statistically significant degree the overall energy expenditure or consumption of the mammal, whereby the total mass of adipocytes in the mammal decreases to a statistically significant degree.

9. A method as recited in claim 7, additionally comprising the step of monitoring the activity of acetyl-CoA carboxylase in adipocytes of the mammal, said monitoring comprising the steps of:

(a) lysing a sample of adipocytes from the mammal;

(b) monitoring the loss of acetyl-CoA or the production of malonyl-CoA in the lysed sample by high performance liquid chromatography or by reverse-phase high performance liquid chromatography.

10. A method as recited in claim 2, additionally comprising the step of monitoring the activity of acetyl-CoA carboxylase in cells of the mammal, said monitoring comprising the steps of:

(a) lysing a sample of cells from the mammal;

(b) monitoring the loss of acetyl-CoA or the production of malonyl-CoA in the lysed sample by high performance liquid chromatography or by reverse-phase high performance liquid chromatography.

* * * * *